(12) United States Patent
Ergler et al.

(10) Patent No.: US 11,197,644 B2
(45) Date of Patent: Dec. 14, 2021

(54) X-RAY IMAGING APPARATUS COMPRISING A DETECTION UNIT WITH A STRAY RADIATION COLLIMATOR

(71) Applicant: Siemens Healthcare GmbH, Erlangen (DE)

(72) Inventors: Thorsten Ergler, Erlangen (DE); Michael Grasruck, Eckental Forth (DE); Barbara Hintz, Erlangen (DE); Peter Kaemmerer, Schnaittach (DE); Carsten Thierfelder, Pinzberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 10 days.

(21) Appl. No.: 16/877,591

(22) Filed: May 19, 2020

(65) Prior Publication Data

US 2020/0375554 A1 Dec. 3, 2020

(30) Foreign Application Priority Data

May 29, 2019 (DE) .......................... 102019207899.0

(51) Int. Cl.
*G21K 1/00* (2006.01)
*A61B 6/06* (2006.01)
(Continued)

(52) U.S. Cl.
CPC ................ *A61B 6/06* (2013.01); *A61B 6/032* (2013.01); *A61B 6/4233* (2013.01)

(58) Field of Classification Search
CPC ......... A61B 6/06; A61B 6/032; A61B 6/4233; A61B 6/4291; G21K 1/02; G21K 1/025; G21K 1/10; G21K 1/04
See application file for complete search history.

(56) References Cited

U.S. PATENT DOCUMENTS

2005/0236574 A1 10/2005 Von Der Haar
2008/0101542 A1 5/2008 Ikhlef et al.
(Continued)

FOREIGN PATENT DOCUMENTS

DE 102004019972 A1 11/2005
JP H11218578 A 8/1999

OTHER PUBLICATIONS

Dr. Thorsten Ergler; Dr. Björn Kreisler; Dr. Steffen Kappler; Dr. Michael Hosemann; Dr. Edgar Ködere, „Pixelgruppen bei Photon-Counting Detektoren, Nov. 28, 2018.

*Primary Examiner* — Don K Wong
(74) *Attorney, Agent, or Firm* — Harness, Dickey & Pierce, P.L.C.

(57) ABSTRACT

An X-ray imaging apparatus includes a detection unit, having an X-ray detector and a stray radiation collimator in stacked arrangement, and an X-ray source opposite the detection unit. The X-ray source is embodied, starting from a focal point, to emit X-rays towards the X-ray detector. The X-ray detector has a sensor plane and is subdivided in a first direction into a plurality of detector elements. Each detector element of the plurality of detector elements is embodied to convert the X-rays impinging on a surface region, assigned to the detector element, of the sensor plane into an electrical pixel measurement signal. The stray radiation collimator has a plurality of collimator walls. The collimator walls are arranged over the surface region of a detector element of the plurality of detector elements, such that a shadow cast by a respective collimator wall completely overlaps with the surface region of the corresponding detector element.

23 Claims, 5 Drawing Sheets

(51) Int. Cl.
*A61B 6/03* (2006.01)
*A61B 6/00* (2006.01)

(56) References Cited

U.S. PATENT DOCUMENTS

2012/0232385 A1 9/2012 Hattori et al.
2013/0121475 A1* 5/2013 Deych .................. G21K 1/00
378/154

* cited by examiner

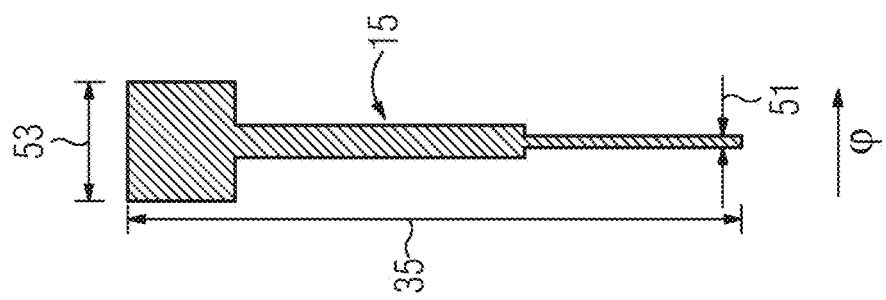
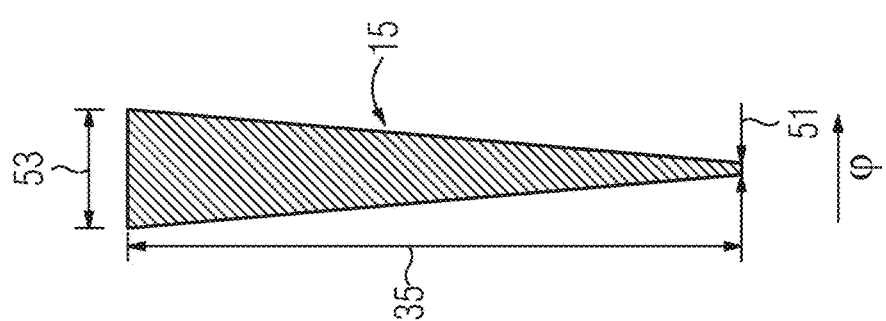
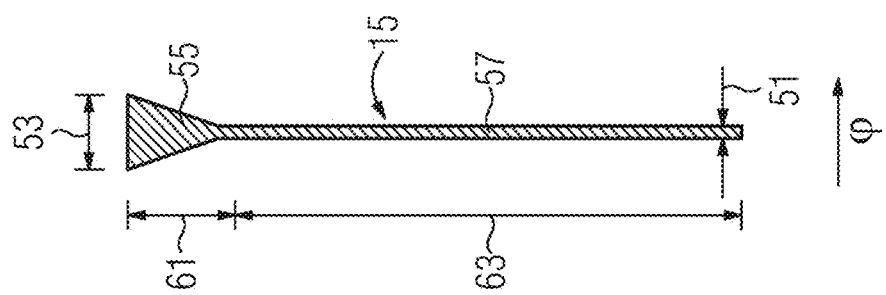
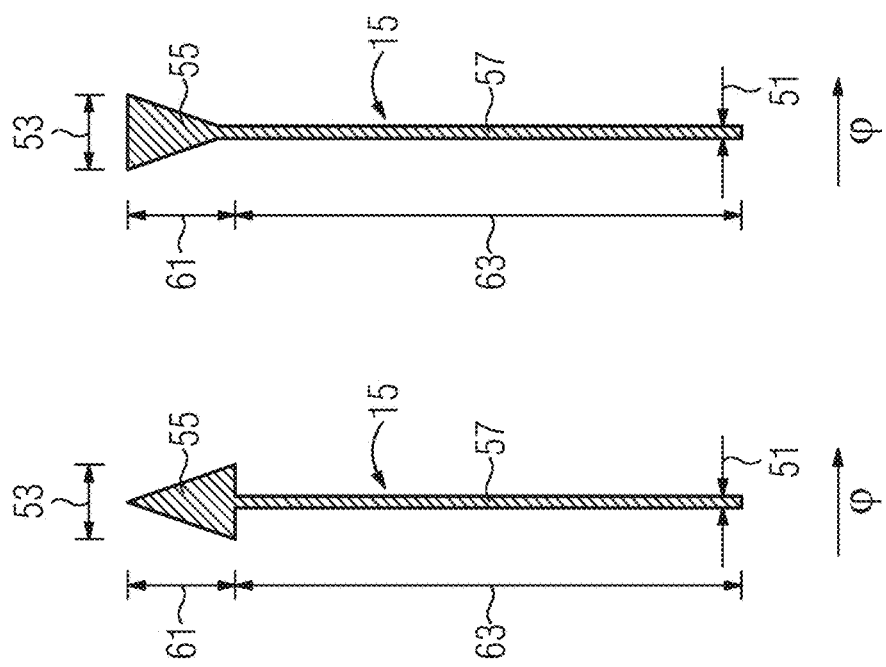
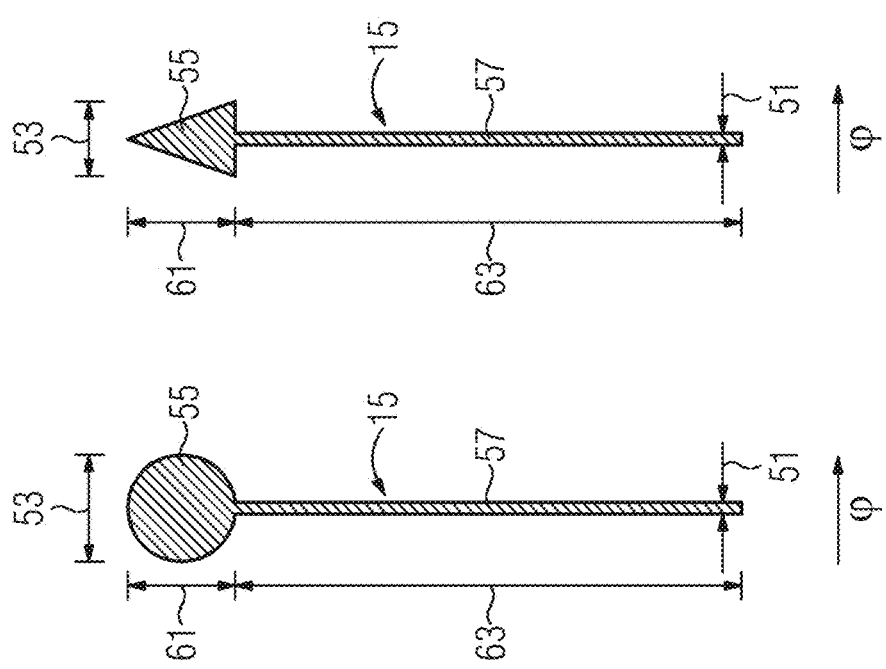

X-RAY IMAGING APPARATUS COMPRISING A DETECTION UNIT WITH A STRAY RADIATION COLLIMATOR

PRIORITY STATEMENT

The present application hereby claims priority under 35 U.S.C. § 119 to German patent application number DE 102019207899.0 filed May 29, 2019, the entire contents of which are hereby incorporated herein by reference.

FIELD

Embodiments of the invention generally relate to an X-ray imaging apparatus comprising a detection unit, having an X-ray detector and a stray radiation collimator in stacked arrangement with the X-ray detector; to a computed tomography system; to a detection unit; and to a stray radiation collimator.

BACKGROUND

X-ray imaging apparatuses generally comprise an X-ray source and, opposite thereto, an X-ray detector. In a computed tomography system in particular, the X-ray source and the X-ray detector are located diametrically opposite on a gantry.

During scanning of an object to be imaged, for example of a patient, the object is positioned in an investigation region of the computed tomography system and the X-ray source and X-ray detector rotate about the object while the X-ray source emits X-rays. The X-rays, which pass through the object, are detected by one or more detector elements, also known as detector pixels, of the X-ray detector and a measurement signal is produced on the basis of the locally detected X-rays. Since, on passing through the object, the X-rays interact and in particular are attenuated depending on local properties of the object, it is in this way possible to draw conclusions as to the properties of the object.

In the case of a computed tomography system, measured projection data for a plurality of angular directions is captured using the X-ray detector during rotational motion of the X-ray source. The measured projection data relates to one projection or a plurality of projections which contain information about the attenuation of the radiation by the object for the respective angular direction. From this data, it is then possible to reconstruct a three-dimensional volume image data set or two-dimensional tomographic image data sets for the object.

Indirect conversion systems may here in particular be used as X-ray detectors. In indirect conversion X-ray detectors, the X-rays may be converted into light by a suitable converter material and into electrical pulses via photodiodes. Scintillators, for example GOS ($Gd_2O_2S$), CsI or other materials, are often used as the converter material. "Indirect conversion X-ray detectors", or "scintillator detectors", are conventionally used in which conversion of the X-ray or gamma radiation into electrical signals proceeds in two stages.

In a first stage, the X-ray or gamma quanta are absorbed in a scintillator element and converted into optically visible light. The light is then converted in a second stage by a first photodiode optically coupled with the scintillator element into an electrical signal, which is then read out by way of evaluation or readout electronics. The individual detector pixels have generally to be separated from one another by septa in scintillation material, wherein "dead zones" are created by the septa and thus by the separating material.

Direct conversion X-ray detectors may moreover also be used. In direct conversion X-ray detectors, the X-rays or photons may be converted into electrical pulses by a suitable converter material. CdTe, CZT, CdZnTeSe, or the like, may for example be used as converter material. The electrical pulses are then assessed by evaluation electronics, for example an integrated circuit (Application Specific Integrated Circuit, ASIC).

To suppress the stray radiation arising on capture, detectors are equipped with stray radiation collimators. In this case, it is conventional for a collimator wall to be arranged next to each detector element. Modern computed tomography systems are in particular equipped with 3D collimators as stray radiation collimators, these substantially having a lattice structure. These 3D collimators enable suppression of the stray radiation in the radial ($\varphi$ direction, direction of rotation) and the axial direction (z direction, perpendicular to direction of rotation). In the past, moreover, stray radiation collimators were also used, which merely provided collimator walls along the axial direction.

SUMMARY

At least one embodiment of the invention provides an advantageous X-ray imaging apparatus with a stray radiation collimator, an advantageous detection unit and an advantageous stray radiation collimator.

Further advantageous and in part per se inventive embodiments and further developments of the invention are described in the claims and the following description.

At least one embodiment of the invention relates to an X-ray imaging apparatus comprising a detection unit, having an X-ray detector and a stray radiation collimator in stacked arrangement with the X-ray detector, and an X-ray source opposite the detection unit. The X-ray source is embodied, starting from a focal point, to emit X-rays towards the X-ray detector. The X-ray detector has a sensor plane and is subdivided at least in a first direction into a plurality of detector elements, wherein each detector element of the plurality of detector elements is embodied to convert the X-rays impinging on a surface region, assigned to the detector element, of the sensor plane into an electrical pixel measurement signal. The stray radiation collimator has a plurality of collimator walls, which are arranged adjacently at least along the first direction, and wherein the collimator walls of the plurality of collimator walls are in each case arranged over the surface region of a detector element of the plurality of detector elements, such that a shadow cast by a respective collimator wall of the plurality of collimator walls onto the sensor plane due to the X-rays completely overlaps with the surface region of the corresponding detector element.

According to a preferred configuration of the X-ray imaging apparatus according to at least one embodiment of the invention, a respective detector element of the plurality of detector elements over which a collimator wall of the plurality of collimator walls is arranged in each case has at least one adjacent detector element over which no collimator wall is arranged.

In one embodiment of the X-ray imaging apparatus according to the invention, the X-ray detector is formed by a plurality of detector modules, in each case having a subset of the plurality of detector elements and which are arranged adjacently along the first direction.

At least one embodiment of the invention relates to an X-ray imaging apparatus comprising:
- a detection unit, the detection unit including
  - an X-ray detector, and
  - a stray radiation collimator in stacked arrangement with the X-ray detector; and
- an X-ray source arranged opposite the detection unit and embodied, starting from a focal point, to emit X-rays towards the X-ray detector,
- the X-ray detector including a sensor plane and being subdivided at least in a first direction into a plurality of detector elements, each respective detector element of the plurality of detector elements being embodied to convert the X-rays impinging on a surface region, assigned to the respective detector element, of the sensor plane into an electrical pixel measurement signal, and
- the stray radiation collimator including a plurality of collimator walls arranged adjacently along the first direction, respective collimator walls of the plurality of collimator walls being respectively arranged over the surface region of a respective detector element of the plurality of detector elements, such that a shadow cast by a respective collimator wall of the plurality of collimator walls onto the sensor plane, due to X-rays, completely overlaps with the surface region of the corresponding respective detector element.

At least one embodiment is directed to a detection unit comprising:
- an X-ray detector; and
- a stray radiation collimator, arranged in stacked arrangement with the X-ray detector, s embodied for use in the X-ray imaging apparatus of an embodiment, wherein
  - the X-ray detector includes a sensor plane and is subdivided at least in a first direction into a plurality of detector elements, each respective detector element of the plurality of detector elements being embodied to convert the X-rays impinging on a surface region, assigned to the respective detector element, of the sensor plane into an electrical pixel measurement signal, and
  - the stray radiation collimator including a plurality of collimator walls, arranged adjacently along the first direction, and the respective collimator walls of the plurality of collimator walls are each respectively arranged over the surface region of a respective detector element of the plurality of detector elements, such that a shadow cast by the respective collimator wall of the plurality of collimator walls onto the sensor plane due to X-rays completely overlaps with the surface region of the corresponding respective detector element.

At least one embodiment is directed to a stray radiation collimator for arrangement in stacked arrangement with an X-ray detector, embodied for use in the detection unit of an embodiment, wherein the stray radiation collimator includes a plurality of collimator walls, arranged adjacently along the first direction, and wherein the respective collimator walls of the plurality of collimator walls are each arranged over the surface region of a respective detector element of a plurality of detector elements of the X-ray detector, such that a shadow cast by a respective collimator wall of the plurality of collimator walls thrown onto the sensor plane due to irradiation with X-rays completely overlaps with the surface region of the corresponding respective detector element.

BRIEF DESCRIPTION OF THE DRAWINGS

The invention is explained below with reference to example embodiments and to the appended figures. The depiction in the figures is schematic, highly simplified and not necessarily true to scale. In the figures:

FIG. 6 to FIG. 10 are each schematic representations of further variants of an example collimator wall of a stray radiation collimator.

DETAILED DESCRIPTION OF THE EXAMPLE EMBODIMENTS

Figure 1:
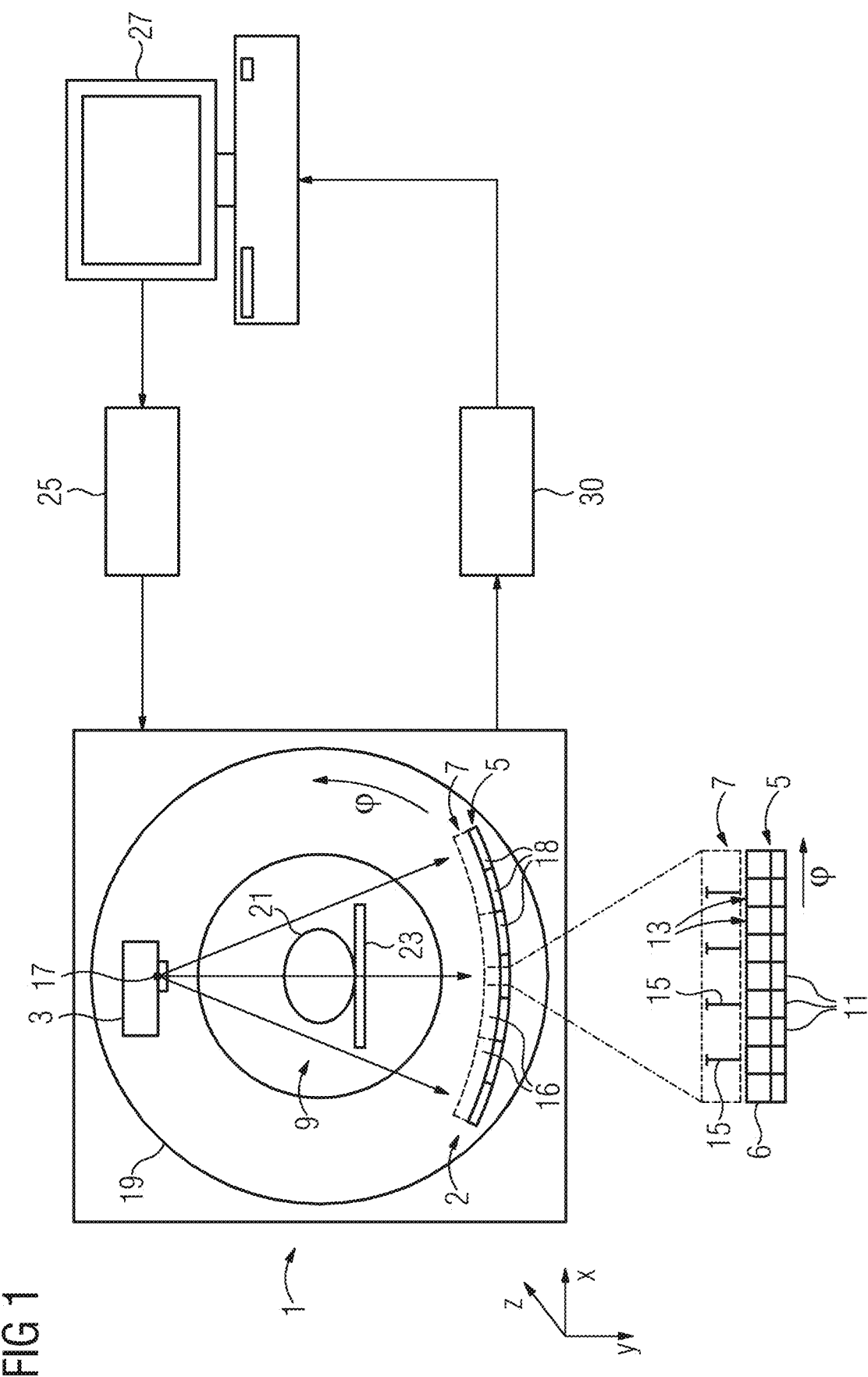
FIG. 1 is a schematic representation of an X-ray imaging apparatus.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an X-ray imaging apparatus comprising a detection unit, having an X-ray detector and a stray radiation collimator in stacked arrangement with the X-ray detector, and an X-ray source opposite the detection unit. The X-ray source is embodied, starting from a focal point, to emit X-rays towards the X-ray detector. The X-ray detector has a sensor plane and is subdivided at least in a first direction into a plurality of detector elements, wherein each detector element of the plurality of detector elements is embodied to convert the X-rays impinging on a surface region, assigned to the detector element, of the sensor plane into an electrical pixel measurement signal. The stray radiation collimator has a plurality of collimator walls, which are arranged adjacently at least along the first direction, and wherein the collimator walls of the plurality of collimator walls are in each case arranged over the surface region of a detector element of the plurality of detector elements, such that a shadow cast by a respective collimator wall of the plurality of collimator walls onto the sensor plane due to the X-rays completely overlaps with the surface region of the corresponding detector element.

The X-ray imaging apparatus is preferably a computed tomography system. The X-ray imaging apparatus may also have another apparatus for capturing X-ray images, for example a C-arm X-ray device.

The X-ray source, in particular an X-ray tube, is embodied to emit X-rays, starting from the focal point, in the form of a fan, a cone or other shape towards the detector. The focal point of the X-ray source may in this case be described in a first approximation as punctiform. As a rule, however, it has a spatial extent. Furthermore, the focal point, or the focal point position, may be variable relative to the X-ray detector or to the stray radiation collimator. The reasons may for example be thermal effects, vibration effects and/or mechanical displacement of the components of the X-ray imaging facility relative to one another during movement of the system, in particular rotation of the gantry in the case of a computed tomography system, during operation of the X-ray imaging apparatus. The focal point may for example have a variable focal point position within a deflection region at least along the first direction relative to the stray radiation collimator. As a result, the relative position of the focal point and of the collimator walls of the plurality of collimator walls relative to one another may vary.

The X-ray detector may be embodied as a direct or indirect conversion X-ray detector. The sensor plane is embodied to convert the X-rays impinging thereon in particular into an electrical measurement signal. In this respect, in an direct conversion X-ray detector, the sensor plane may comprise in particular the converter material, for example CdTe or CdZTe. In an indirect conversion X-ray detector, the sensor plane may in this respect comprise the combination of scintillation material and downstream photodiode.

The X-ray detector is here subdivided at least along the first direction into a plurality of detector elements, also known as pixels. It may moreover also be subdivided into detector elements in a second direction extending perpendicular to the first direction. That is to say, the X-ray detector has at least one line of detector elements along the first direction. Moreover, a plurality of such lines may for example be arranged adjacently along the second direction. In the case of a computed tomography system, the first direction preferably corresponds to the direction of rotation of the system.

One surface region of the sensor plane is assigned to each detector element. The pixel measurement signal generated by a respective detector element of the plurality of detector elements during acquisition is then based substantially on those X-rays which impinge on the surface region of the respective detector element, or are absorbed in the sensor volume, defined by this surface region, of the sensor plane. The surface region is in general also designated an active surface of a detector element or pixels. The pixel measurement signals of the plurality of detector elements may then be further processed by downstream read-out and evaluation electronics. On the basis of the pixel measurement signals of the plurality of detector elements, or the further processing thereof, a spatially resolved image data set may then be generated.

In addition to the active surface or the active surfaces of the plurality of detector elements, the X-ray detector may have "dead zones", which are not assigned to any detector element or which do not contribute to a pixel measurement signal or measurement signals generated in these regions are possibly excluded from the further processing. Dead zones are formed, for example, by the septa between two detector elements in the scintillation material of a scintillator detector. Dead zones may for example also be embodied by second detector elements which are inactive or not used for further processing or result from an anode structure varied in this region in the case of direct conversion X-ray detectors.

Arrangement of the stray radiation collimator in stacked arrangement with the X-ray detector is intended substantially to describe a relative arrangement of the two elements in the direction of the incident radiation. That is to say, the stray radiation collimator is arranged substantially over the X-ray detector, i.e. upstream of the X-ray detector in the direction of emission of the X-rays, also known as direction of ray incidence. In particular, the stray radiation collimator is arranged downstream of an object to be imaged in the direction of ray incidence. In particular, the stray radiation collimator may be arranged in the spatial vicinity of the X-ray detector. In this case, the stray radiation collimator may be in direct contact with the X-ray detector and be fastened to the X-ray detector or may also have no direct contact with the X-ray detector.

The collimator walls of the plurality of collimator walls may be substantially flat. The collimator walls of the plurality of collimator walls may have an extent substantially in the direction of the surface normal of the sensor plane or preferably in the direction of the incident X-rays, i.e. in the direction of ray incidence. This extent is hereinafter denoted wall height of a collimator wall of the plurality of collimator walls. The collimator walls moreover have an extent along the first direction. The extent of a collimator wall of the plurality of collimator walls along the first direction is hereinafter denoted wall thickness.

The collimator walls of the plurality of collimator walls may preferably be substantially aligned with the focal point of the X-ray source, such that unscattered X-rays leaving from the focal point can impinge unimpeded between the collimator walls onto the sensor plane.

According to at least one embodiment of the invention, the collimator walls are arranged adjacent one another along the first direction. In this case, the stray radiation collimator substantially forms a grating structure. Passage channels between the collimator walls for the incident X-rays, delimited by the collimator walls, are then defined merely on two sides along the first direction. The stray radiation collimator may however additionally have further collimator walls in other variant configurations, which collimator walls are arranged adjacently and perpendicular to the first direction. The stray radiation collimator may thus have a three-dimensional lattice structure, wherein the passage channels defined by the collimator walls of the plurality of collimator walls and the further collimator walls are accordingly delimited both in the direction perpendicular to the first direction and in the direction along the first direction by collimator walls.

The plurality of collimator walls preferably includes tungsten as material. The plurality of collimator walls may however also include lead, molybdenum, zinc or another material whose X-ray absorption behavior leads to sufficient suppression of stray radiation.

According to at least one embodiment of the invention, one collimator wall of the plurality of collimator walls is in each case arranged over the surface region assigned to a detector element of the plurality of detector elements, in such a way that the shadow cast by the respective collimator wall due to the X-rays falls merely onto the surface region of the respective detector element, i.e. leads, within the surface region of a respective detector element, to shading of the sensor plane. This means the projection of a collimator wall of the plurality of collimator walls starting from the focal point and along the direction of the irradiated X-rays is located wholly within the surface region of that detector element over which the collimator wall is arranged. The term casting a shadow or shading is here understood to mean that part of the sensor plane is thereby described on which no X-rays can impinge due to a collimator wall.

Owing to the shadow cast by a collimator wall onto a surface region of a detector element, the pixel measurement signal is reduced relative to an unshaded detector element with the same intensity of impinging X-rays.

In the prior art, to achieve a maximally shade-free structure, the collimator walls are conventionally positioned over a dead zone of the detector, i.e. in the case of a scintillator for example over a septum between two detector elements. One challenge for the structure/design of the stray radiation collimators consists in the fact that, taking account of all structural tolerances and focal movements of the tube, the shadow is as far as possible always or at least largely intercepted in the dead zone. However, to keep dose losses through these dead zones low, it is desirable for the dead zones to have a maximally small extent. The smaller the detector elements and thus the collimator structures, the more stringent become the requirements for the tolerances of the stray radiation collimators or the structure and the positioning thereof relative to the dead zones. To ensure a maximally shadow-free structure, it is necessary for a stray radiation collimator to be precisely positioned and fixed on the detector. The costs of such collimators are likewise high.

By the positioning of the collimator walls being decoupled, according to at least one embodiment of the invention, from the dead zones, for example septa, and positioning instead proceeding relative to the surface region of a respective detector element of the plurality of detector elements, production and positioning tolerances may advantageously be relaxed. For example, positioning no longer proceeds with regard to a septum between two detector elements with an extent in the range from ~80 μm, but rather relative to a surface region with an extent in the range from ~1-1.2 mm. In this way, the absolute position tolerances may in this example be enlarged by a factor ~10.

It is therefore also conceivable to design the collimator walls to be thicker. That is to say, the wall thickness of the collimator walls of the plurality of collimator walls may be selected to be greater along the first direction than, for example, the extent of a dead zone. The choice of wall thickness may proceed independently of the extent of the dead zone. The greater wall thickness, for example in the range from ~200-300 μm, may facilitate the use of other, possibly less expensive manufacturing technologies. The stray radiation collimator may be embodied as an injection molding, for example. Other manufacturing technologies may however also be used.

Positioning of the collimator walls over the active surface region of detector elements of the plurality of detector elements additionally offers the advantage that dynamic changes to how the shadow is cast and thus any concomitant temporal fluctuations in the pixel measurement signal in the shaded detector element may be mapped into or intercepted in one and the same detector element. The focal point of the X-ray source may have a variable focal point position within a deflection range along the first direction and relative to the collimator walls. The change in focal point position then leads to projection, i.e. a shadow being cast, which varies locally and/or with regard to extent, of the collimator walls along the first direction onto the sensor plane. A variable focal point position may be caused by vibration effects, rotation effects or control fluctuations of the focal point of the X-ray tube. A wall positioned next to or between two detector elements may have an effect on both adjoining detector elements, wherein the extent of the effect is in each case temporally variable.

According to a preferred configuration of the X-ray imaging apparatus according to at least one embodiment of the invention, a respective detector element of the plurality of detector elements over which a collimator wall of the plurality of collimator walls is arranged in each case has at least one adjacent detector element over which no collimator wall is arranged.

It may be provided that a collimator wall of the plurality of collimator walls is arranged solely over the surface region in each case of an n-th detector element of the plurality of detector elements. In this case, n is greater than two, preferably greater than three. In this variant configuration, for example, a collimator wall is positioned solely over each fourth detector element.

The surface region of a respective detector element of the plurality of detector elements in each case has an areal extent along the first direction. If the detector elements of the plurality of detector elements are of substantially identical structure, the distance between two adjacent collimator walls of the plurality of collimator walls along the first direction in this configuration may then correspond to an integral multiple of the areal extent along the first direction.

The wall height of the collimator walls of the plurality of collimator walls in the direction of ray incidence is here preferably selected as a function of the distance between two adjacent collimator walls of the plurality of collimator walls.

Enlarging the distance between two adjacent collimator walls may reduce the suppression effect with regard to stray radiation. Increasing the wall height may increase the suppression effect of the stray radiation. A ratio of wall height to distance, the "grid ratio", of the collimator walls of at least 10 to 1 or more is preferably selected.

Material- and thus cost-saving production may advantageously be enabled.

In one advantageous configuration of the X-ray imaging apparatus according to at least one embodiment of the invention, the surface region of a respective detector element of the plurality of detector elements has an areal extent along the first direction, wherein the areal extent of the surface region of a detector element of the plurality of detector elements over which a collimator wall of the plurality of collimator walls is arranged is greater than the areal extent of the surface region of a detector element of the plurality of detector elements over which no collimator wall is arranged.

Since, for detector elements of the plurality of collimator walls over which a collimator wall is arranged, a larger active surface is provided, i.e. a greater extent of the surface regions assigned to these detector elements, shading and thus the dose loss caused by the collimator walls may advantageously be wholly or partly compensated. Such adaptation of the detector elements must be combined with an image reconstruction based on the pixel measurement signals of the detector elements.

According to one particularly preferred variant of the X-ray imaging facility according to at least one embodiment of the invention, each collimator wall of the plurality of collimator walls has a first wall thickness along the first direction on a first side facing the X-ray detector and a second wall thickness along the first direction on a second side remote from the X-ray detector and the X-ray source. According to at least one embodiment of the invention, in this variant embodiment the second wall thickness is greater than the first wall thickness.

The first wall thickness may preferably represent the minimum extent of the respective collimator wall of the plurality of collimator walls. The second wall thickness may preferably represent the maximum extent of the respective collimator wall of the plurality of collimator walls.

The second wall thickness is preferably at least twice as great as the first wall thickness. It may however also be selected to be less than twice as great.

The second wall thickness may be formed at an upper top, facing the incident X-rays, of a respective collimator wall of the plurality of collimator walls of the stray radiation collimator. It is preferably formed at least in the spatial vicinity of the upper top. The first wall thickness may be formed at a lower bottom of the stray radiation collimator facing the sensor plane. It is preferably formed at least in the spatial vicinity of the lower bottom.

The passage channels for X-rays defined by the collimator walls of the plurality of collimator walls have inlet openings remote from the X-ray detector and outlet openings for X-rays facing the X-ray detector. In the above-described configuration, the inlet openings then accordingly have a smaller surface than the outlet openings. The extent of the inlet openings along the first direction is here determined by the second wall thickness. The extent of the outlet openings along the first direction is determined by the first wall thickness.

The positioning according to at least one embodiment of the invention of a respective collimator wall of the plurality of collimator walls over the surface region assigned to a detector element of the plurality of detector elements advantageously enables signal fluctuations of the pixel measurement signal caused by changes to the shadow cast to take effect only within an individual pixel. However, it is advantageous to keep signal fluctuations which arise as a result of changes to the shadow cast to as low a level as possible even within one detector element, in order to avoid possible effects on imaging by the X-ray imaging apparatus.

The shadow cast by a respective collimator wall onto the sensor plane corresponds with the projection of the collimator wall starting from the focal point and in the direction of ray incidence. If the focal point of the X-ray source changes relative to the collimator wall, for example due to rotation effects or control fluctuations of the focal point position, a temporally dynamic variation of the projection in location and extent of the projection onto the sensor plane may occur. In the case of a purely local variation of the shadow cast within an individual surface region, no significant temporal fluctuation of the pixel measurement signal outlet by a detector element is to be expected. On the other hand, a dynamic variation of the extent of the shadow cast leads to a temporal signal fluctuation of the pixel measurement signal.

By way of the second wall thickness, which according to this configuration is greater than the first wall thickness, it is in particular advantageously possible to reduce the temporal variation of the extent of the shadow cast by a collimator wall in the first direction. The inventors have recognized that, since the second wall thickness is greater than the first wall thickness, the influence of the second wall thickness on the projection, resulting from the X-rays, of the respective collimator wall onto the sensor plane may be intensified. On the other hand, the influence of the wall height of a respective collimator wall on the shadow cast may be reduced, or may even be wholly avoided depending on the embodiment. In this way, the temporal variation of the extent of the shadow cast may be reduced. Compared to a typical structure, the dependency of the extent of the shadow cast on the geometric position or the orientation of the respective collimator wall may be reduced relative to the instantaneous focal point position. A temporal variation of the pixel measurement signal by temporal variation of the shadow cast may thus advantageously be reduced.

If the second wall thickness is selected to be correspondingly great, even a substantially constant extent of the shadow cast by a collimator wall may be achieved despite a varying focal point position relative to the collimator wall. A substantially constant pixel measurement signal may thus be produced.

Although the selection of a second wall thickness which is greater than the first wall thickness leads on average to increased shading and thus to a lower dose efficiency of the system than a constant wall thickness, on the other hand possible effects of temporal signal fluctuations of individual pixels on the imaging may, however, be reduced. Moreover, calibration routines may advantageously better be used for adjustment of the pixel measurement signals in order to compensate the signal attenuation of detector elements affected by shading relative to unaffected detector elements.

If the focal point of the X-ray source has a focal point position, variable relative to the stray radiation collimator within a deflection region along the first direction, the second wall thickness may then preferably be embodied as a function of the deflection region in such a way that the shadow cast by a respective collimator wall of the plurality of collimator walls onto the sensor plane is determined at least for the major part of the focal point positions within the deflection region solely by projection of the second wall thickness in the direction of the emitted X-rays onto the sensor plane.

In particular, the shadow cast by a collimator wall is then not influenced for the major part of the focal point positions by projection of the wall height of the collimator wall onto the sensor plane or by a lower edge, facing the X-ray detector, of the collimator wall.

The deflection region along the first direction of the focal point position of the focal point of the X-ray source relative to the collimator walls of the plurality of collimator walls may for example be determined by rotation effects or control fluctuations of the focal point.

The major part of the focal point positions may in this case in particular comprise the region of the deflection region in which the focal point is to be found with a statistical probability of at least 50%, preferably of at least 70%, still more preferably of at least 90%.

The stray radiation collimator may also be embodied, i.e. the second wall thickness may be selected to be correspondingly large, such that, for the entire deflection range, the shadow cast by a respective collimator wall of the plurality of collimator walls onto the sensor plane is determined by the projection of the second wall thickness in the direction of the emitted X-rays onto the sensor plane. In this case, a substantially constant pixel measurement signal may be achieved as a function of focal point position in an affected detector element.

The geometric arrangement of the stray radiation collimator in the X-ray detector apparatus and a configuration of the collimator walls with a second wall thickness which is greater than the first wall thickness may be used to keep approximately constant the extent of the projection of a respective collimator wall onto the sensor plane even in the case of a varying focal point position along the first direction or at least to reduce variations as a function of focal point position. At the same time, the effect of the shadow cast is in each case restricted to an individual detector element. Advantageous dynamic signal fluctuations caused by varying shading may thus be reduced by a variable focal point position.

In one further advantageous embodiment of the X-ray imaging apparatus, a gap which is more permeable to X-rays is formed between the plurality of collimator walls and the sensor plane of the X-ray detector.

In particular, the X-ray-permeable gap is embodied such that X-ray radiation emitted by the X-ray source may be irradiated beneath at least one subset of the plurality of collimator walls if the focal point position corresponds to a peripheral position within the above-described deflection region of the focal point. A peripheral position may then accordingly be described as a position which is not numbered among the above-described major part of the focal point positions.

This means that it is possible, in particular when the focal point adopts extreme positions, for X-rays from the X-ray source to arrive unscattered on the sensor plane in a region directly below a respective collimator wall.

X-ray-permeable may mean that the gap is free of material. A material may however also be provided which has only a minor effect on the impinging X-rays, for example a plastic.

Such an embodiment may enable the selection of a second wall thickness which is smaller compared to an embodiment without a gap, without having to dispense with smoothing of the temporal variation of the pixel measurement signal by the variable focal point position. This may advantageously contribute to the dose efficiency of the apparatus, since less shading may be achieved.

According to one advantageous variant of the X-ray imaging apparatus according to at least one embodiment of the invention, each collimator wall in each case has an extent along the first direction which tapers continuously or in stepped manner over the wall height from the second wall thickness to the first wall thickness.

The collimator wall may have a substantially conical cross-section. The second wall thickness may in this case determine the maximum extent of the conical cross-section and the first wall thickness may define the minimum extent of the conical cross-section. The collimator wall may also have a different, continuously tapering cross-section.

The collimator wall may have a cross-section tapering in stepped manner. For example, a respective collimator wall has a plurality of successive wall portions, for example five or seven, with different wall thicknesses. In this case, the wall portion which is closest to the X-ray detector has the first wall thickness and the wall portion which is furthest away from the X-ray detector has the second wall thickness. Other embodiments are also possible.

Collimator walls with high stability may advantageously be provided.

Alternatively, according to a further advantageous variant of the X-ray imaging apparatus according to the invention, each collimator wall of the plurality of collimator walls includes a head element having the second wall thickness and a foot element having the first wall thickness.

In this embodiment, a respective collimator wall of the plurality of collimator walls may in particular comprise two wall portions, wherein the foot element corresponds to a first wall portion and the head element corresponds to a second wall portion. The first wall portion is in this respect arranged closer to the X-ray detector in the direction of ray incidence than the second wall portion. The head element is embodied in particular on the side remote from the X-ray detector and facing the incident radiation. The head element may define the shape and extent of an upper top of a respective collimator wall which faces the incident X-rays. The foot element is embodied on the side of a respective collimator wall facing the X-ray detector. The foot element may define the shape and extent of a lower bottom of the respective collimator wall which faces the sensor plane.

The first wall portion, i.e. the foot element, extends in particular over a first partial height of the wall height of a respective collimator wall of the plurality of collimator walls. The second wall portion, i.e. the head element, extends in particular over a second partial height of the wall height. In this case, the head element, i.e. the second wall portion, preferably assumes a smaller, particularly preferably a markedly smaller second partial height than the first partial height. The first partial height may comprise at least 50%, preferably at least 80%, of the wall height.

The head element may have the second wall thickness at an upper top of the head element facing the incident X-rays which faces the incident X-rays. The second wall thickness may however also be offset relative to the upper top surface. The head element has the second wall thickness in particular as a maximum extent of the head element along the first direction.

The foot element may have the first wall thickness in particular as minimum extent of the foot element along the first direction.

The head element and the foot element may have a constant cross-sectional extent, i.e. a constant wall thickness, over the corresponding partial heights thereof. In this embodiment, the head element and the foot element have a substantially rectangular cross-section. The foot element and/or the head element may however also have a different cross-section.

The foot element and the head element may be connected seamlessly to one another.

The foot element and the head element may preferably include the same material. They may also include a different material.

Advantageously, a particularly simple structure of a collimator wall with a greater second wall thickness may be implemented.

Advantageously, a collimator wall structure which is maximally economical with regard to materials may be implemented.

In one advantageous variant of the X-ray imaging apparatus according to the invention, the head element in particular has a trapezoidal, rhomboidal, triangular, circular, elliptical or rectangular cross-section with a maximum extent along the first direction corresponding to the second wall thickness.

In one embodiment of the X-ray imaging apparatus according to the invention, the X-ray detector is formed by a plurality of detector modules, in each case having a subset of the plurality of detector elements and which are arranged adjacently along the first direction.

A detector module may in each case comprise at least one or more sensor units, which in each case provide a sub-region of the sensor plane. A respective detector module preferably in each case comprises a multiplicity of detector elements. A detector module may in each case comprise at least one or more evaluation unit(s) for read-out and evaluation of the pixel measurement signals. A detector module of the plurality of detector modules may in particular be understood to be a structural unit. A detector module may in particular comprise detector module fastener(s). By way of the detector module fastener(s), the detector modules may for example be fastened to a module retainer of the detection unit next to one another along the first direction. The X-ray detector is subdivided, for example, into more than 16 detector modules.

It may be provided that the stray radiation collimator is formed by a plurality of collimator modules, which are arranged adjacently along the first direction and in stacked arrangement with the X-ray detector.

A collimator module may in particular in each case have a subset of the plurality of collimator walls. A collimator module may in particular be understood as a structural unit, including module fastener(s) for fastening the collimator modules in the X-ray imaging apparatus and relative to the X-ray detector. The collimator modules may be fastened to the X-ray detector. A collimator module may also not be fastened to the X-ray detector, i.e. not be in contact with the X-ray detector, but merely be fastened relative thereto in the detection unit, for example to a housing of the detection unit, or in the X-ray imaging apparatus. A collimator module may moreover comprise a supporting structure which fixes the collimator walls together and ensures stability of the arrangement during operation of the X-ray imaging apparatus.

Subdivision into detector modules or collimator modules may advantageously simplify not only production and relative positioning relative to one another but also assembly of the X-ray imaging apparatus.

In one preferred embodiment of the X-ray imaging apparatus according to the invention, a collimator module of the plurality of collimator modules extends in each case over more than one detector module along the first direction. In this embodiment, one collimator module is assigned to more than one detector module. For example, one collimator module extends along the first direction over two, three or four detector modules.

Through the positioning of the collimator walls over the surface regions of the detector elements, relaxation of the absolute assembly tolerances is achieved with regard to the septa or dead zones. It is thereby more simply possible to produce and position collimator modules within the tolerances, such that larger structural units can also be better used. This advantageously enables simplified production and cost-saving production of the detection unit.

Furthermore, one advantageous variant of the X-ray imaging apparatus provides that the distance between two adjacent collimator walls is greater in the case of a peripherally arranged collimator module of the plurality of collimator modules than in the case of a centrally arranged collimator module.

Centrally substantially means assigned to the central region of the X-ray detector along the first direction. The central region comprises the region in the spatial environment of the central ray of the X-rays emitted by the X-ray source. For example, the central region comprises the central 20% to 70% of the extent of the X-ray detector along the first direction. For example, the central region of an X-ray detector constructed from detector modules comprises the central 6-12 detector modules. A centrally arranged collimator module may then be assigned to one or more of the central X-ray detector modules. A peripherally arranged collimator module is accordingly arranged in a peripheral region of the stray radiation collimator, wherein the peripheral region is located away from the central region along the first direction.

The collimator walls of a centrally arranged collimator module are for example arranged in stacked arrangement over the surface region of every third detector element. For example, the collimator walls of a peripherally arranged collimator module are arranged in stacked arrangement with the X-ray detector over the surface region of every fifth detector element. Other embodiments are also possible.

One particularly cost-effective variant, which is also economical with regard to materials, of the stray radiation collimator and thus of the X-ray imaging apparatus according to at least one embodiment of the invention is thereby advantageously enabled.

Furthermore, one advantageous variant of the X-ray imaging apparatus provides that the collimator walls of a peripherally arranged collimator module of the plurality of collimator modules have a wall height which is different from the wall height of the collimator walls of a centrally arranged collimator module.

The collimator walls of a peripherally arranged module may have a lower wall height. A particularly cost-saving structure is advantageously possible.

Alternatively, a greater wall height is also feasible for collimator walls of a peripherally arranged collimator module. In combination in particular with an enlarged distance of the collimator walls in the case of collimator walls of a peripherally arranged collimator module, the suppressing action for stray radiation reduced by the enlarged distance may be partly or wholly compensated by a greater wall height. A peripheral collimator module has the same grid ratio in the case of a greater distance between the collimator walls as a centrally arranged collimator module with a smaller distance between the collimator walls.

Furthermore, one advantageous variant of the X-ray imaging apparatus provides that the collimator walls of a peripherally arranged collimator module of the plurality of collimator modules include a material with a lower absorption coefficient for X-rays than the collimator walls of a centrally arranged collimator module.

For example, a peripheral collimator module may have collimator walls of zinc. For example, a centrally arranged collimator module may have collimator walls of tungsten. In particular, a more favorable material may be used. A particularly cost-effective variant of the stray radiation collimator and thus of the X-ray imaging apparatus according to at least one embodiment of the invention is thereby advantageously enabled.

The decoupling of X-ray detector and stray radiation collimator, or of the collimator walls from the position and embodiment of dead zones, advantageously enables a significantly greater latitude with regard to designs and combinations of designs for the stray radiation collimator.

At least one embodiment of the invention further relates to an X-ray imaging apparatus of an embodiment, wherein the X-ray imaging apparatus is a computed tomography system.

The above-described advantages and variant embodiments of the above-described X-ray imaging apparatus are in this respect applicable to the computed tomography system.

Furthermore, at least one embodiment of the invention relates to a detection unit including an X-ray detector and a stray radiation collimator in stacked arrangement with the X-ray detector, which is embodied for use in an X-ray imaging apparatus according to at least one embodiment,
- wherein the X-ray detector has a sensor plane and is subdivided at least in a first direction into a plurality of detector elements, wherein each detector element of the plurality of detector elements is embodied to convert the X-rays impinging on a surface region, assigned to the detector element, of the sensor plane into an electrical pixel measurement signal,
- the stray radiation collimator has a plurality of collimator walls, which are arranged adjacently along the first direction, and wherein the collimator walls of the plurality of collimator walls are in each case arranged over the surface region of a detector element of the plurality of detector elements, such that a shadow cast by a respective collimator wall of the plurality of collimator walls onto the sensor plane due to irradiation with X-rays completely overlaps with the surface region of the corresponding detector element.

Furthermore, at least one embodiment of the invention relates to a stray radiation collimator for arrangement in stacked arrangement with an X-ray detector, which is embodied for use in a detection unit of an X-ray imaging apparatus according to the subject matter of at least one embodiment, wherein the stray radiation collimator has a plurality of collimator walls which are arranged adjacently along the first direction, and wherein the collimator walls of the plurality of collimator walls are in each case arranged over a surface region of a detector element of the plurality of detector elements of the X-ray detector, such that a shadow cast by a respective collimator wall of the plurality of collimator walls due to irradiation with X-rays onto the sensor plane completely overlaps with the surface region of the corresponding detector element.

All variant embodiments which have been described above in the context of the X-ray imaging apparatus according to the invention may accordingly also be embodied in the detection unit or the stray radiation collimator alone. The description made with regard to the X-ray imaging apparatus and the previously described advantages of the X-ray imaging apparatus according to at least one embodiment of the invention may accordingly also be applied to the detection unit according to at least one embodiment of the invention and to the stray radiation collimator according to at least one embodiment of the invention.

FIG. 1 is a schematic representation of one example of an X-ray imaging apparatus 1. The X-ray imaging apparatus 1 corresponds, in the case shown, to a computed tomography system. The X-ray imaging apparatus 1 has an X-ray source 3, for example an X-ray tube, and opposite thereto a detection unit 2, which comprises an X-ray detector 5 and a stray radiation collimator 7 in stacked arrangement with the X-ray detector.

The X-ray source 3 and the detection unit 2 are arranged diametrically on the gantry 19, which is rotatable by way of a pivot bearing apparatus about a system axis in the direction of the z axis. The direction of rotation is labeled $\varphi$ in the figure. The X-ray source 3 is embodied to emit X-rays 9. An object 21 may be positioned between the X-ray source 3 and the detection unit 2 on an object bearing unit 23, for example a patient table, along the system axis in an investigation region 4 for scanning with X-rays 9.

During rotation, the radiation source 3 emits the X-rays 9, in the shape of a fan, cone or the like, starting from a focal point 17 towards the detection unit 2, such that measured projection data is collected from a plurality of directions so as to prepare on the basis thereof a plurality of projection images or a three-dimensional volume image of the region of the object 21 to be imaged.

The X-rays 9 which the object 21 transmits are detected by way of the X-ray detector 5. Various embodiments of the X-ray detector 5 are possible. The X-ray detector 5 may be embodied as a direct conversion X-ray detector 5 with a sensor plane 6 including a corresponding converter material, for example CdTe, which is embodied to convert the impinging X-rays 9 into an electrical measurement signal. The X-ray detector may in particular be embodied as an indirect conversion X-ray detector 5 in the form of a scintillation detector, having a sensor plane 6 comprising a scintillation plane combined with downstream connected photodiodes, which are embodied to convert the light generated in the scintillation material by the X-rays 9 into an electrical measurement signal.

A part of the detection unit 2, including the stray radiation collimator 7 and the X-ray detector 5, is depicted schematically and on an enlarged scale for illustrative purposes.

The X-ray detector 5 with the sensor plane 6 has a plurality of detection elements 11, in general also known as pixels. Substantially one surface region 13 of the sensor plane 6 of the X-ray detector 5 is assigned to each detector element 11 of the plurality of detector elements 11. Each detector element 11 is embodied to convert the X-rays 9 impinging on the assigned surface region 13 or absorbed in this region of the sensor plane 6 into a corresponding pixel measurement signal.

The X-ray detector 5 is subdivided at least along a first direction $\varphi$ into the plurality of detector elements 11. That is to say, the plurality of detector elements 11 form at least one detector row along the first direction $\varphi$. In the case illustrated, the first direction $\varphi$ corresponds to the direction of rotation of the computed tomography system. Moreover, the X-ray detector 5 may also be subdivided along a second direction into a plurality of detector elements 11. The depicted X-ray detector 5 may for example have a plurality of detector rows arranged next to one another in the z direction. In the case of the depicted computed tomography system the X-ray detector preferably comprises a plurality of detector rows along the z direction, such that at least 1-3 cm or an even larger region of the object may simultaneously be scanned in the direction of the z axis by way of the X-ray detector 5.

The stray radiation collimator 7, indicated by the collimator walls 15, is arranged in stacked arrangement with the X-ray detector 5. The stray radiation collimator 7 serves to absorb stray radiation, which may impair the quality of captured X-ray images, in particular the signal-to-noise ratio, such that it no longer reaches the sensor plane 6. Stray radiation here in particular means those X-rays which are scattered or deflected on passage through the object 21 and/or at parts of the object 21 or of the X-ray imaging apparatus 1. In contrast, primary radiation denotes X-rays 9 which reach the X-ray detector 5 from the X-ray source 3 substantially unscattered.

The stray radiation collimator 7 is arranged between the X-ray detector 5 and the X-ray source 3 and in the direction of ray incidence downstream of the object 21 to be imaged. In stacked arrangement here means that it is in particular arranged in the spatial vicinity of the X-ray detector 5 and, in the direction of ray incidence, in front of, i.e. over, the X-ray detector 5. The stray radiation collimator may be arranged in direct contact with the X-ray detector 5 or without contact with the X-ray detector 5. The stray radiation collimator 7 may be firmly connected with the X-ray detector 5. For example, the stray radiation collimator 7 is fastened to the X-ray detector 5. The stray radiation collimator 7 may however also not be fastened to the X-ray detector 5.

The detection unit 2 may moreover for example comprise a housing, which partly or wholly surrounds the X-ray detector 5 and/or the stray radiation collimator 7. For example, the stray radiation collimator 7 may then also be fastened to a housing part and, by arranging the X-ray detector 5 in or relative to the housing, a stacked arrangement of the stray radiation collimator 7 and of the X-ray detector 3 may be achieved.

The stray radiation collimator 7 comprises a plurality of collimator walls 15. These are in particular arranged adjacent one another along the first direction φ. In the example shown, the stray radiation collimator 7 has adjacent collimator walls 15 solely along the first direction φ. It is conceivable, however, in variant embodiments for further collimator walls to be arranged adjacent one another also along a second direction, here in the z direction. This may be deemed sensible if a stray radiation suppression effect along the second direction is also desired.

The collimator walls 15 shown substantially delimit passage channels for the X-rays 9, preferably for the primary radiation, with an inlet opening facing the X-ray source 3 and an outlet opening facing the X-ray detector 5.

As indicated in the enlarged portion, the collimator walls 15 of the plurality of collimator walls 15 of the stray radiation collimator 7 are arranged according to the invention over the X-ray detector 5 in such a way that the collimator walls 15 are each arranged over the surface region of a detector element 11 of the plurality of detector elements 11, such that a shadow 45, 47, 145, 147, 245, 247 cast by a respective collimator wall 15 of the plurality of collimator walls 15 onto the sensor plane 6 due to the X-rays 9 completely overlaps with the surface region 13 of the corresponding detector element 11 over which the respective collimator wall 15 is arranged.

That is to say, the collimator walls 15 are arranged such that a projection of a respective collimator wall 15 of the plurality of collimator walls 15 onto the sensor plane 6 by the X-rays 9 and along the direction of ray incidence in each case falls wholly within an individual surface region 13 of a detector element 11 of the plurality of detector elements 11.

By the positioning of the collimator walls 15 being decoupled, according to the invention, from dead zones, for example septa, and positioning instead proceeding relative to the surface region 13 of a respective detector element 11 of the plurality of detector elements 11, production and positioning tolerances may advantageously be relaxed. It is moreover conceivable to make the collimator walls 15 thicker. An increase in wall thickness must be balanced with the dose efficiency of the X-ray imaging apparatus 1, i.e. with the signal loss in the detector element 11 due to shading. However, the use of other, possibly less expensive manufacturing technologies may thereby be facilitated. The stray radiation collimator 7 may be embodied as an inexpensive injection molding, for example.

The positioning of the collimator walls 15 over the active surface of detector elements 11 of the plurality of detector elements 11 additionally offers the advantage that dynamic variations in the shadow cast and thus any concomitant temporal fluctuations in the pixel measurement signal in the shaded detector element, for example due to vibration effects, rotation effects or control fluctuations of the focal point of the X-ray tube, are mapped to or intercepted in one and the same detector element 15, it not being the case, as it is in conventional prior art arrangements, that two detector elements may be affected by focal point variations to a temporally varying extent between the active surfaces of two detector elements.

The collimator walls 15 of the plurality of collimator walls 15 for example include tungsten, lead, molybdenum, or indeed a different material, which allows the proportion of stray radiation incident onto the sensor plane 6 to be reduced to a sufficiently significant extent, by the collimator walls 15 absorbing it. The plurality of collimator walls 15 are preferably aligned with the focal point of the X-ray source, such that unscattered X-rays 9, i.e. the primary radiation, may pass unimpeded through the stray radiation collimator to the sensor plane 6.

In the example shown of the computed tomography system, pixel measurement signals which have been produced by the X-ray detector 5 in response to the impinging X-rays 9 and optionally also aggregated and further processed by way of further data processing units into measured projection data, are output to a reconstruction unit 30, which reconstructs three-dimensional volume image data or two-dimensional tomographic image data of the object 21 on the basis of the pixel measurement signals or the corresponding projection measurement data based thereon by using a suitable analytical, iterative, or other reconstruction algorithm.

The image data may then be displayed to an operator by way of a monitor 27. The monitor 27 may likewise display a user interface, and a computer, which is connected with the monitor 27, may be embodied to acquire a user input, for example by clinical staff. The user input may then be translated by way of a control unit 25 into instructions for units of the X-ray imaging apparatus 1, for example for the X-ray detector 5, the X-ray source 3 or other apparatus units, and forwarded, such that capture parameters can be adapted for the capture of image data by way of the X-ray imaging apparatus 1. The computer may likewise be embodied to acquire a user input to the reconstruction unit 30 and forward it to enable the adaptation of reconstruction parameters.

In one embodiment of the X-ray imaging apparatus 1, the X-ray detector 5 is formed from a plurality of detector modules 18. For illustrative purposes, the figure shows just seven detector modules 18. For example, the X-ray detector 5 is assembled from 16, 32 or more detector modules 18, arranged adjacently along the first direction φ. A detector module 18 in each case comprises a subset of the plurality of detector elements. Each detector module in particular comprises a multiplicity of detector elements 11. The detector modules 18 may in each case form a structural unit, which may be mounted next to one another on a module holder by way of detector module fastener(s) formed on the detector modules 18 in order to form the X-ray detector 5.

Likewise, according to one embodiment, the stray radiation collimator 7 is assembled from a plurality of collimator modules 16 which are arranged adjacently along the first direction φ. The schematic figure indicates just three collimator modules 16 for illustrative purposes. The stray radiation collimator may however be composed of more than three collimator modules 16. A collimator module 16 of the plurality of collimator modules 16 then in each case comprises a subset of the plurality of collimator walls 15. Each collimator module 16 in this case preferably comprises a multiplicity of collimator walls 15.

The number of detector modules 18 and collimator modules 16 depicted are selected merely for illustrative purposes. In particular, more than the depicted detector modules 18 and collimator modules 16 may be adjacently arranged.

According to a preferred embodiment of the X-ray imaging apparatus 1, one collimator module 16 extends, in the example shown, more than one detector module 18 along the first direction φ. In the example shown, one collimator module 16 in each case extends over two or three detector modules 18. In other embodiments, one collimator module 16 may also extend over four or more detector modules 18.

The stray radiation collimator 7 preferably has adjacent collimator walls 15 merely along the first direction φ. The positioning of the collimator walls over the surface regions leads to shading of the active surfaces and thus to a reduced dose efficiency of the X-ray detector apparatus 1. One option for compensating the reduced dose utilization due to the shadow cast due to positioning over the active surfaces of the detector elements may be achieved in that, in contrast with currently conventional 3D collimators, the stray radiation collimator merely has collimator walls which are arranged adjacently along the first direction. By omitting collimator structures perpendicular to the first direction, the dose efficiency of the X-ray detector according to the invention may sometimes be increased. Such an embodiment appears particularly sensible in particular in the case of X-ray detectors with a small extent perpendicular to the first direction. This applies in particular in comparison with "thick-footed" collimators. An existing option for avoiding temporally dynamic casting of shadows due to a varying focal point consists in "thick-footed" or "thick-walled" structures, wherein a lower wall portion broader than an upper wall portion and partly overlapping with the active region of the pixel, i.e. looking out over a dead zone, is constructed on a side facing the X-ray detector of a wall placed over a dead zone, of such a thick-footed collimator, such that dynamic casting of shadows by the wall, extending beyond the dead zone itself, may be intercepted by the "thick-footed" region. In this way, it may be ensured that the projection of a wall of the stray radiation collimator onto the sensor plane is substantially unchanged in position and extent. However, shading of the active surface also takes place.

Figure 2:
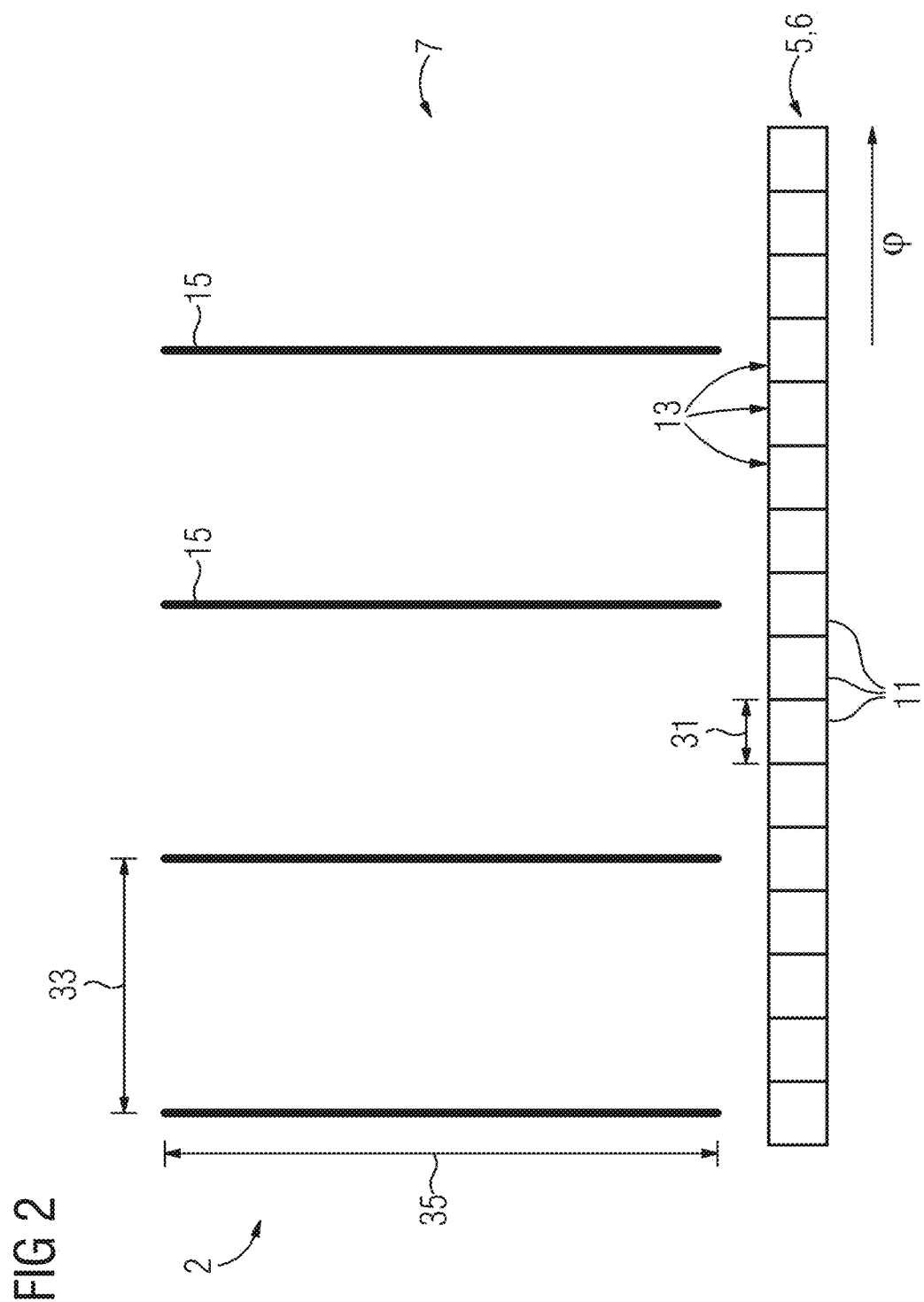
FIG. 2 is a schematic representation of a portion of a detection unit with an X-ray detector and a stray radiation collimator in a stacked arrangement in a cross-sectional representation.

FIG. 2 shows a further enlarged, schematic cross-sectional representation of part of a detection unit 2 with an X-ray detector 5 having a sensor plane 6 and a stray radiation collimator 7 in stacked arrangement with the X-ray detector 5.

In this example, the collimator walls 15 are arranged over every fourth detector element 11, i.e. over their respective surface region 13 of every fourth detector element 11. Thus, every detector element 11 over which a collimator wall 15 is arranged has at least one adjacent detector element 11 along the first direction φ over which no collimator wall 15 is arranged. The respective surface region 13 of the depicted detector elements 11 has an areal extent 13 along the first direction φ. The collimator walls 15 of the plurality of collimator walls 15 each have a distance 33 from one another. The distance 33 corresponds in the depicted embodiment to a multiple, in particular an integral multiple, of the areal extent 31.

In the depicted variant, the detector elements 11 each have the same surface area 31 along the first direction φ. In another variant configuration of the X-ray imaging apparatus 1 according to the invention it may be provided that the areal extent 31 along the first direction φ is greater for one detector element 11 of the plurality of detector elements 11 over which a collimator wall 15 of the plurality of collimator walls is arranged than the areal extent 31 of a detector element 11 over which no collimator wall 15 of the plurality of collimator walls is arranged. In this way, dose losses due to shading of the surface regions by the collimator walls may optionally be compensated or reduced.

The collimator walls 15 additionally have a wall height 35 along the direction of ray incidence. With a greater distance 33, a correspondingly greater wall height 35 is advantageous, such that the grid ratio remains constant, such that a substantially uniform suppression effect is ensured for stray radiation.

In the variant of the detection unit 2 as depicted in FIG. 1, in which the stray radiation collimator 7 is composed of a plurality of collimator modules 16, it is conceivable that, in the case of the peripherally arranged collimator modules 16 of the plurality of collimator modules 16, the distance 33 between two adjacent collimator walls 15 is greater than in the case of the centrally arranged collimator module 16. In the case shown in FIG. 1, the stray radiation collimator 7 has a centrally arranged collimator module 16, which may be assigned to the central region of the X-ray detector 5, and two peripheral collimator modules 16.

Another embodiment of the detection unit 2 may provide that the collimator walls 15 of the peripherally arranged collimator modules 16 of the plurality of collimator modules 16 have a different wall height 35 from the wall height 35 of the collimator walls 15 of the centrally arranged collimator module 16. The wall height may preferably be lower. Variants are however also possible in which a peripherally arranged collimator module 16 has a higher wall height 35, in particular in combination with a greater distance 33 between the collimator walls 15 of the peripheral collimator modules 16 than the centrally arranged collimator module 16.

Another embodiment may provide that the collimator walls 15 of the peripherally arranged collimator modules 16 of the plurality of collimator modules 16 include material with a lower absorption coefficient for the X-rays 9 than the collimator walls 15 of the centrally arranged collimator module 16. For example, the centrally arranged collimator module includes tungsten as material and the peripheral collimator modules 16 include zinc.

The differentiation between centrally arranged collimator modules 16 and peripherally arranged collimator modules 16 enables a reduction in cost and manufacturing effort. In the above-described embodiments, it is in some cases necessary to accept that this is associated with a reduced suppression effect for stray radiation in the peripheral regions of the X-ray detector 5. In many cases of application of the X-ray imaging apparatus 1, however, the peripheral regions are less relevant to imaging, such that cost-efficiency and the need for the suppression effect can be weighed up against one another and a corresponding design selected. Relaxing assembly and manufacturing tolerances by placing the collimator walls independently of dead zones advantageously opens up the possibility for greater latitude with regard to designs and combinations and in particular also less expensive embodiments of the apparatus according to the invention.

Figure 3:
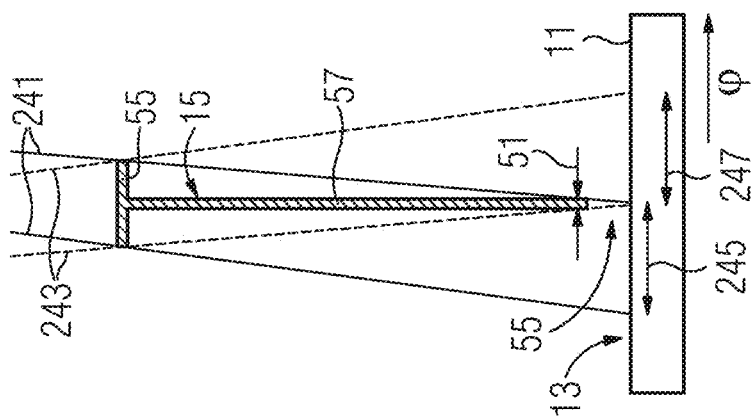
FIG. 3 to FIG. 5 are each schematic representations of an example collimator wall of a stray radiation collimator in various variants and the resultant shadow cast onto the sensor plane.

FIG. 3 schematically illustrates, on the basis of an example collimator wall 15 of the plurality of collimator walls 15, the shadow 45, 47 cast by the collimator wall 15 onto the surface region 13 of that detector element 11 over which the collimator wall 15 is arranged by the X-rays 9 emitted by the X-ray source 3.

As already described, the positioning according to the invention of a respective collimator wall 15 of the plurality of collimator walls 15 over the surface region 13 assigned to a detector element 11 of the plurality of detector elements 11 advantageously enables signal fluctuations of the pixel measurement signal caused by changes to the shadow cast to take effect only within an individual detector element. However, it is moreover advantageous to keep signal fluctuations which arise as a result of changes to the shadow cast to as low a level as possible even within one detector element 11, in order to avoid possible effects on imaging by the X-ray imaging apparatus 1.

The shadow cast by the collimator wall 15 shown in FIG. 3 results from the projection of the collimator wall 15 onto the surface region 13 starting from the focal point 17 of the X-ray source 3. The resultant projection along the first direction φ for a first focal point position of the focal point 17 is indicated by the lines 41. The resultant projection for a second focal point position of the focal point 17 is indicated by the lines 43. The extents 45 and 47 in each case reflect the resultant extents of the projection, i.e. the extents of the shadow cast, onto the surface region 13 assigned to the detector element 11. The resultant projection onto the surface region 13, i.e. the resultant shadow cast, in each case completely overlaps with the surface region 13, i.e. the active surface, of the detector element 11. A varying focal point 17 is always intercepted in such a way in an individual detector element, provided the extent of the shadow cast does not exceed the extent of the active surface. In contrast thereto, a collimator wall arranged next to or between two detector elements may lead to a temporally varying shadow being cast in the two adjoining detector elements.

Depending on focal point position, the extent 45, 47 of the projection, i.e. of the shadow cast, by the collimator wall is different in this variant embodiment, however. The first focal point position results in a greater extent 45 of the shadow cast onto the surface region 13 than the second focal point position, which results in a smaller extent 47 of the shadow cast onto the surface region 13. That is to say, depending on focal point position, a different extent of a detector element 11 is shaded, so resulting in a temporally dynamic variation in the extent of the shadow cast and thus of the pixel measurement signal detected by way of the detector element 11. Projection of the collimator wall 15 onto the surface region by the incident X-rays corresponds substantially to the projection of the wall height 35 onto the sensor plane 6.

Figure 4:
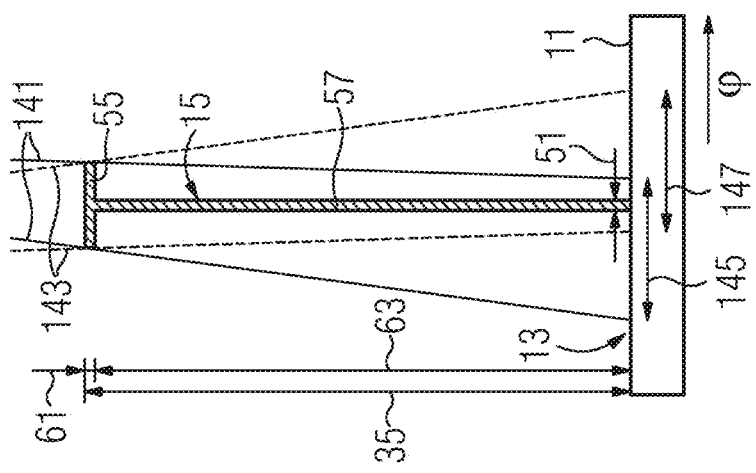

FIG. 4 likewise schematically illustrates the shadow cast by an example collimator wall 15 of the plurality of collimator walls 15 according to a second variant embodiment of the collimator wall 15. The variant depicted here may advantageously serve to reduce or wholly avoid a varying extent of the shadow cast within the surface region 13 of a detector element 11. The example collimator wall 15 to this end has a first wall thickness 51 along the first direction φ on a side of the collimator wall 15 facing the X-ray detector 5, here represented by the detector element 11. The example collimator wall 15 moreover has a second wall thickness 53 on a side of the collimator wall 15 remote from the X-ray detector 5. The second wall thickness 53 is greater than the first wall thickness 51.

In the variant embodiment depicted, the example collimator wall is formed by way of a foot element 57 having the first wall thickness 51 and a head element 55 having the second wall thickness 53. The foot element 57 extends over a first partial height 63 of the wall height 35 and the head element over a second partial height 61 of the wall height, wherein the second partial height 61 is smaller than the first partial height 63. In this example, the head element and the foot element have a substantially rectangular cross-section.

The resultant projection, i.e. the resultant shadow cast, by a collimator wall 15 embodied in this way onto the surface region 13 by the X-rays 9 emitted by the X-ray source 3 for a first focal point position of the focal point 17 is indicated by the lines 141. The resultant projection of a collimator wall 15 embodied in this way onto the surface region 13 by the X-rays 9 emitted by the X-ray source 3 for a second focal point position of the focal point 17 is indicated by the lines 143.

In the cases shown, the projection of the collimator wall 15 onto the surface region 13, i.e. onto the sensor plane 6, by the X-rays 9 is substantially determined by the projection of the second wall thickness 53 onto the surface region 13. The respective extent 145, 147 of the projection along the first direction, i.e. the extent 145, 147 of the shadow cast, is in this case virtually independent of the geometric position or orientation of the collimator wall 15 relative to the focal point position assumed. On the other hand, the local position of the shadow cast within the surface region 13 varies. That is to say, the shadow profile produced of the collimator wall 15 migrates with the focal point position. The overall signal attenuation, caused by the shading, of the pixel measurement signal relative to an unshaded detector element is expected to be approximately identical, however, for both the first and the second focal point positions.

If the focal point of the X-ray source 3 has a focal point position, variable relative to the stray radiation collimator 7 within a deflection region along the first direction φ, the second wall thickness 53 may be embodied as a function of the deflection region in such a way that the shadow cast by a respective collimator wall 15 of the plurality of collimator walls 15 onto the sensor plane 6 is determined for all the focal point positions within the deflection region solely by projection of the second wall thickness 53 in the direction of the emitted X-rays 9 onto the sensor plane 6. A substantially constant pixel measurement signal of a shaded detector element 11 may thereby advantageously also be achieved in the case of varying focal point positions. In other embodiments, the second wall thickness 53 may also be selected such that the signal fluctuations are at least reduced as a function of the deflection region of the focal point 17.

Figure 5:
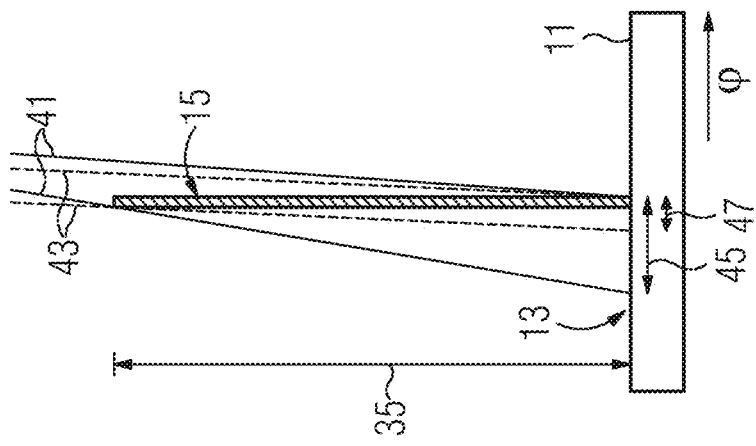

FIG. 5 is a schematic representation of the shadow cast by an example collimator wall 15 of the plurality of collimator walls 15 illustrated according to a third variant embodiment.

The example collimator wall 15 depicted shows a similar structure to that described in FIG. 4. However, an X-ray-permeable gap 55 is formed between the stray radiation collimator 7, represented by the example collimator wall 15, and the X-ray detector 5, represented by the example detector element 11.

For specific focal point positions relative to the example collimator wall 15, the X-ray-permeable gap allows X-rays 9 emitted by the X-ray source 3 to be irradiated beneath the collimator wall 15. This applies in this case in particular for unscattered X-rays 9, i.e. for primary radiation of the X-ray source 3.

In particular, the X-ray-permeable gap 55 is embodied such that X-ray radiation emitted by the X-ray source 3 may be irradiated beneath at least one subset of the plurality of collimator walls 15 if the focal point position corresponds to a peripheral position within the above-described deflection region of the focal point 17.

For extreme positions of the focal point relative to the collimator walls, i.e. for example for peripheral positions of the focal point within the deflection region of the focal point relative to the collimator walls along the first direction φ, or in the case of an excessively small second wall thickness 53 as a function of the deflection region of the focal point 17, the projection of the collimator wall 15 onto the surface region 13 may be influenced by a lower edge of the collimator wall. In this way, a temporal signal fluctuation dependent on the temporal variation in focal point position may be brought about for these peripheral regions.

If, for example, in FIG. 5 no sufficiently large X-ray-permeable gap 55 was formed, but rather the foot element 57 was formed right down to the detector element 11, the resultant projection of the collimator wall 15 and in particular the extent thereof on the sensor plane would be influenced by the lower edge of the collimator wall 15 depending on the relative position of the focal point 17 relative to the collimator wall 15.

This effect could be ruled out by a greater second wall thickness 53. A greater second wall thickness 53 leads, however, to greater shading and thus to a lower dose efficiency of the detection unit 2.

As an alternative to a greater second wall thickness 53, the X-ray-permeable gap 55, which allows unscattered X-rays 9 to be irradiated beneath the collimator wall 15, makes it possible to diminish the above-described effect and thus to avoid a temporal signal fluctuation as a function of focal point position relative to collimator wall 15.

The X-ray-permeable gap 55 ensures that the extents 245, 247 of the shadow cast by the collimator wall 15 due to the X-rays 9 is solely determined for the focal point positions shown here by projection of the second wall thickness 53 onto the example surface region 13. The influence of a lower edge of the collimator wall 15 is avoided.

One disadvantage of an X-ray-permeable gap 55 would be that the suppression effect for stray radiation would likewise be reduced at this point. Compared with the signal variations caused by a varying extent of the shadow cast, however, this effect may be disregarded in a first approximation.

FIGS. 6 to 10 each show further different variant embodiments of an example collimator wall 15 of an X-ray imaging apparatus 1 according to the invention with a first wall thickness 51 and a second wall thickness 53, wherein the second wall thickness 53 is greater than the first wall thickness 51.

FIGS. 6 to 8 show alternative variant embodiments of the example collimator wall 15 shown in FIGS. 4 and 5 with a foot element 57 which extends over a first partial height 63 and a head element 55 which extends over a second, smaller partial height 61. The first wall portion corresponding to the foot element is in this case arranged closer to the X-ray detector 3 in the direction of ray incidence than the second wall portion, corresponding to the head element.

In this case, the head element 55 in the example embodiments shown has different cross-sections, wherein the maximum extent of the head element 53 along the first direction φ in each case corresponds to the second wall thickness 53.

FIG. 6 shows an example collimator wall 15 with a head element 55, which has a circular cross-section. The second wall thickness 53 in this case corresponds to the diameter of the circle. The foot element shows a rectangular cross-section, having the first wall thickness 51. FIGS. 7 and 8 show further variants with a substantially triangular cross-section of the head element 53. Other embodiments, for example rhomboidal or droplet-shaped, are additionally also possible.

The head element 55 may in this case have the second wall thickness 53 at an upper top of the head element facing the incident X-rays 9 or the collimator wall 15 facing the incident X-rays, as illustrated by way of example in FIGS. 4, 5 and 7. The second wall thickness 53 may however also be slightly offset relative to the upper top, as for example in FIG. 6 and FIG. 7. The second wall thickness 53 is preferably formed in the spatial vicinity of the upper top.

In other embodiments, the foot element 57 may also have a cross-section deviating from a rectangular cross-section shown here by way of example. The foot element 57 may also have a slightly conical cross-section.

In these examples, the head element 55 and the foot element 57 include the same material, for example tungsten. They may however also include different materials.

FIGS. 9 and 10 show further variants of an example collimator wall 15. In these variant embodiments, the respective example collimator wall 15 has a wall thickness along the first direction which tapers over the wall height 35 from the second wall thickness 53 to the first wall thickness 51.

FIG. 9 shows a continuously tapering wall thickness. In this variant embodiment, the example collimator wall 15 has a conical cross-section, wherein the maximum extent along the first direction corresponds to the first wall thickness 53 and the minimum extent to the first wall thickness 15.

FIG. 10 shows a wall thickness which tapers in steps, over three wall portions, each having a different wall thickness, wherein the wall portion arranged closest to the X-ray detector has the first wall thickness 51, and the wall portion furthest away from the X-ray detector has the second wall thickness 53. The number of three wall portions is selected merely by way of example.

Figure 11:
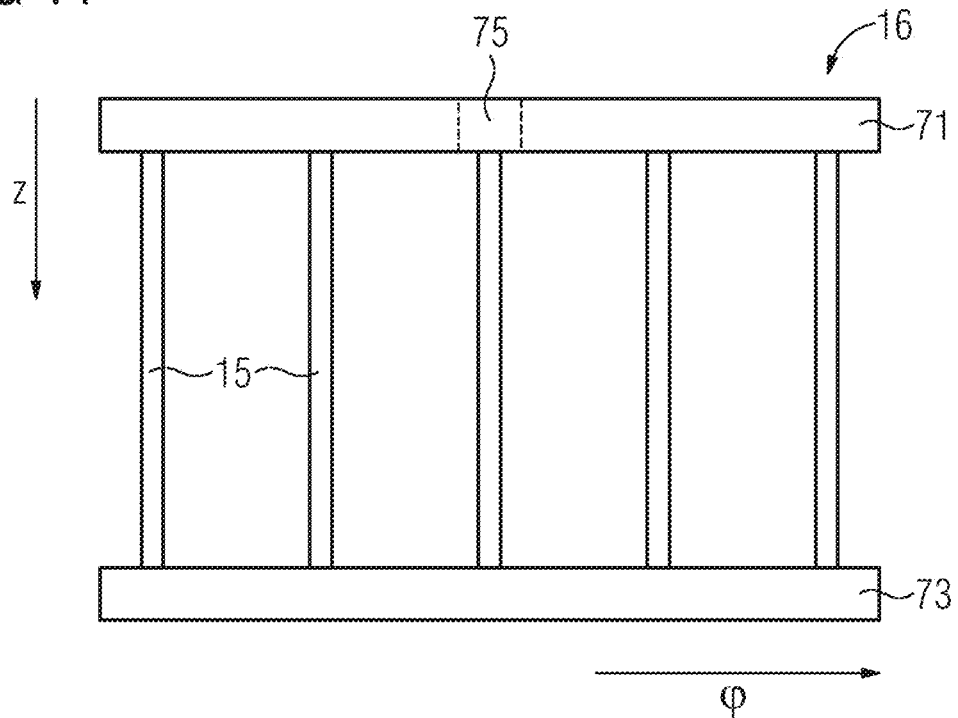
FIG. 11 is a schematic representation of a collimator module of a stray radiation collimator in a plan view.
Figure 12:
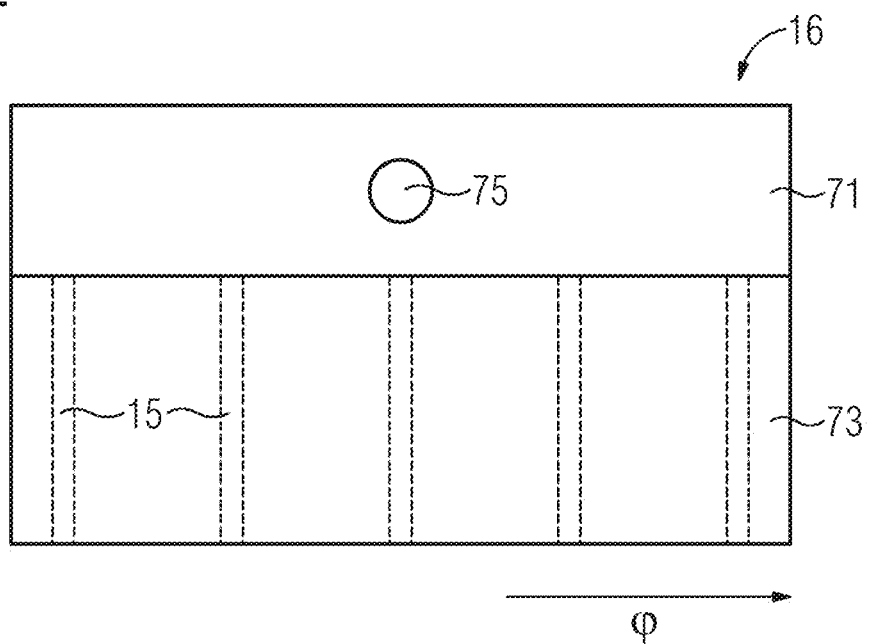
FIG. 12 is a schematic representation of a collimator module of a stray radiation collimator in a side view.

FIGS. 11 and 12 show an example embodiment of a collimator module in plan view (FIG. 11) and side view (FIG. 12). The number of the collimator walls 15 shown should be understood to be stated merely by way of example and is selected for illustrative purposes.

The collimator walls are fixed relative to one another by way of a supporting structure 71, 73 attached on both sides. One of the two units of the supporting structure 71 moreover has a module fastener 75.

If the position and extent of the collimator walls 15 is no longer coupled to the septum geometry or the geometry of a differently configured dead zone, the collimator wall may also be designed to be wider than this, for example the wall thickness may amount to ~150-350 μm. In this case, other manufacturing technologies may also be used.

It would also be conceivable to fixedly incorporate, for example to adhesively bond, relatively thick tungsten sheets into a mechanical housing.

On the basis of the example embodiment shown in FIGS. 10 and 11, the one of the units of the supporting structure 71 including the module fastener(s) 75 may form a surface for screwing to a housing of the detection unit. In general, such a structure may be embodied as an injection molding, wherein both the collimator walls and the supporting structures 71, 73 may be produced in one operation.

The present invention is not limited to the above-described example embodiments. Rather, a person skilled in the art is capable of deriving further embodiments of the invention from the above description. In particular, the individual features of the invention described with reference to the various example embodiments and the variant embodiments thereof may also be combined together in different ways.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray imaging apparatus comprising:
a detection unit, the detection unit including
an X-ray detector, and
a stray radiation collimator in stacked arrangement with the X-ray detector; and
an X-ray source arranged opposite the detection unit and embodied, starting from a focal point, to emit X-rays towards the X-ray detector,
the X-ray detector including a sensor plane and being subdivided at least in a first direction into a plurality of detector elements, each respective detector element of the plurality of detector elements being embodied to convert the X-rays impinging on a surface region, assigned to the respective detector element, of the sensor plane into an electrical pixel measurement signal, and
the stray radiation collimator including a plurality of collimator walls arranged adjacently along the first direction, respective collimator walls of the plurality of collimator walls being respectively arranged over the surface region of a respective detector element of the plurality of detector elements, such that a shadow cast by a respective collimator wall of the plurality of collimator walls onto the sensor plane, due to X-rays, completely overlaps with the surface region of the corresponding respective detector element.

2. The X-ray imaging apparatus of claim 1, wherein a respective detector element of the plurality of detector elements, over which a respective collimator wall of the plurality of collimator walls is arranged, includes at least one adjacent detector element, of the plurality of detector elements, over which no collimator wall is arranged.

3. The X-ray imaging apparatus of claim 1, wherein the surface region of a respective detector element of the plurality of detector elements, includes an areal extent along the first direction and wherein the areal extent of a respective detector element of the plurality of detector elements, over which a collimator wall of the plurality of collimator walls is arranged, is relatively greater than the areal extent of a respective detector element of the plurality of detector elements over which no collimator wall is arranged.

4. The X-ray imaging apparatus of claim 1, wherein each respective collimator wall of the plurality of collimator walls includes a first wall thickness along the first direction on a first side facing the X-ray detector and a second wall thickness on a second side remote from the X-ray detector, and wherein the second wall thickness is relatively greater than the first wall thickness.

5. The X-ray imaging apparatus of claim 4, wherein the focal point of the X-ray source includes a focal point position, variable relative to the stray radiation collimator within a deflection region along the first direction.

6. The X-ray imaging apparatus of claim 4, wherein each respective collimator wall of the plurality of collimator walls includes a wall height in the direction of the impinging X-rays, and each respective collimator wall includes an extent along the first direction which tapers continuously or in stepped manner over the wall height from the second wall thickness to the first wall thickness.

7. The X-ray imaging apparatus of claim 4, wherein each respective collimator wall of the plurality of collimator walls includes a head element, including the second wall thickness along the first direction, and a foot element, including the first wall thickness, along the first direction.

8. The X-ray imaging apparatus of claim 7, wherein the head element includes a trapezoidal, rhomboidal, triangular, circular, elliptical or rectangular cross-section with a maximum extent along the first direction corresponding to the second wall thickness.

9. The X-ray imaging apparatus of claim 1, wherein a gap, which is relatively more permeable to X-rays, is formed between the plurality of collimator walls and the sensor plane of the X-ray detector.

10. The X-ray imaging apparatus of claim 1, wherein the X-ray detector is embodied by a plurality of detector modules, each of the plurality of detector modules including a subset of the plurality of detector elements arranged adjacently along the first direction, wherein the stray radiation collimator is embodied by a plurality of collimator modules arranged adjacently along the first direction and in stacked arrangement with the X-ray detector, and wherein a respective collimator module of the plurality of collimator modules extends over more than one detector module of the plurality of detector modules along the first direction.

11. The X-ray imaging apparatus of claim 1, wherein the stray radiation collimator is embodied by a respective plurality of collimator modules, arranged adjacently along the first direction and in stacked arrangement with the X-ray detector, including a respective subset of the plurality of collimator walls, and wherein
 a distance between two adjacent collimator walls is relatively greater in a case of a peripherally arranged collimator module of the plurality of collimator modules than in a case of a centrally arranged collimator module of the plurality of collimator modules, or
 the collimator walls of a peripherally arranged collimator module of the plurality of collimator modules (16) includes a different wall height from a wall height of the collimator walls of a centrally arranged collimator module of the plurality of collimator modules, or
 the collimator walls of a peripherally arranged collimator module of the plurality of collimator modules include a material with a relatively lower absorption coefficient for the X-rays than the collimator walls of a centrally arranged collimator module of the plurality of collimator modules.

12. The X-ray imaging apparatus of claim 1, wherein the X-ray imaging apparatus is a computed tomography system.

13. A detection unit comprising:
 an X-ray detector; and
 a stray radiation collimator, arranged in stacked arrangement with the X-ray detector, embodied for use in the X-ray imaging apparatus of claim 1, wherein
  the X-ray detector includes a sensor plane and is subdivided at least in a first direction into a plurality of detector elements, each respective detector element of the plurality of detector elements being embodied to convert the X-rays impinging on a surface region, assigned to the respective detector element, of the sensor plane into an electrical pixel measurement signal, and
  the stray radiation collimator including a plurality of collimator walls, arranged adjacently along the first direction, and the respective collimator walls of the plurality of collimator walls are each respectively arranged over the surface region of a respective detector element of the plurality of detector elements, such that a shadow cast by the respective collimator wall of the plurality of collimator walls onto the sensor plane due to X-rays completely overlaps with the surface region of the corresponding respective detector element.

14. A stray radiation collimator for arrangement in stacked arrangement with an X-ray detector, embodied for use in the detection unit of claim 12, wherein the stray radiation collimator includes a plurality of collimator walls, arranged adjacently along the first direction, and wherein the respective collimator walls of the plurality of collimator walls are each arranged over the surface region of a respective detector element of a plurality of detector elements of the X-ray detector, such that a shadow cast by a respective collimator wall of the plurality of collimator walls thrown onto the sensor plane due to irradiation with X-rays completely overlaps with the surface region of the corresponding respective detector element.

15. The X-ray imaging apparatus of claim 2, wherein the surface region of a respective detector element of the plurality of detector elements, includes an areal extent along the first direction and wherein the areal extent of a respective detector element of the plurality of detector elements, over which a collimator wall of the plurality of collimator walls is arranged, is relatively greater than the areal extent of a respective detector element of the plurality of detector elements over which no collimator wall is arranged.

16. The X-ray imaging apparatus of claim 2, wherein each respective collimator wall of the plurality of collimator walls includes a first wall thickness along the first direction on a first side facing the X-ray detector and a second wall thickness on a second side remote from the X-ray detector, and wherein the second wall thickness is relatively greater than the first wall thickness.

17. The X-ray imaging apparatus of claim 5, wherein the second wall thickness is embodied as a function of the deflection region in such a way that the shadow cast by a respective collimator wall of the plurality of collimator walls onto the sensor plane is determined, at least for the major part of the focal point positions within the deflection region, solely by projection of the second wall thickness in the direction of the emitted X-rays onto the sensor plane.

18. The X-ray imaging apparatus of claim 16, wherein the focal point of the X-ray source includes a focal point position, variable relative to the stray radiation collimator within a deflection region along the first direction.

19. The X-ray imaging apparatus of claim 18, wherein the second wall thickness is embodied as a function of the deflection region in such a way that the shadow cast by a respective collimator wall of the plurality of collimator walls onto the sensor plane is determined, at least for the major part of the focal point positions within the deflection region, solely by projection of the second wall thickness in the direction of the emitted X-rays onto the sensor plane.

20. The X-ray imaging apparatus of claim 5, wherein each respective collimator wall of the plurality of collimator walls includes a wall height in the direction of the impinging X-rays, and each respective collimator wall includes an extent along the first direction which tapers continuously or in stepped manner over the wall height from the second wall thickness to the first wall thickness.

21. The X-ray imaging apparatus of claim 5, wherein each respective collimator wall of the plurality of collimator walls includes a head element, including the second wall thickness along the first direction, and a foot element, including the first wall thickness, along the first direction.

22. The X-ray imaging apparatus of claim 2, wherein a gap, which is relatively more permeable to X-rays, is formed between the plurality of collimator walls and the sensor plane of the X-ray detector.

23. The X-ray imaging apparatus of claim 2, wherein the X-ray imaging apparatus is a computed tomography system.

\* \* \* \* \*